US008802444B1

(12) United States Patent  
McElhanon et al.

(10) Patent No.: US 8,802,444 B1  
(45) Date of Patent: Aug. 12, 2014

(54) DETECTION OF ELECTROPHILIC AND NUCLEOPHILIC CHEMICAL AGENTS

(75) Inventors: James R. McElhanon, Albuquerque, NM (US); Timothy J. Shepodd, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 13/553,959

(22) Filed: Jul. 20, 2012

Related U.S. Application Data

(60) Division of application No. 11/983,500, filed on Nov. 9, 2007, now Pat. No. 8,247,554, and a continuation of application No. 11/416,667, filed on May 2, 2006, now Pat. No. 7,449,579.

(51) Int. Cl.  
*G01N 21/64* (2006.01)  
*C07D 491/00* (2006.01)

(52) U.S. Cl.  
USPC ............................................ 436/172; 546/90

(58) Field of Classification Search  
USPC ......................................................... 436/172  
See application file for complete search history.

(56) References Cited

U.S. PATENT DOCUMENTS

| 7,449,579 | B1 | 11/2008 | McElhanon et al. |
| 7,700,040 | B2 * | 4/2010 | Thomas et al. ................ 422/52 |
| 7,897,402 | B2 * | 3/2011 | Thomas et al. ................ 436/98 |
| 7,910,058 | B2 * | 3/2011 | Thomas et al. ................ 422/52 |
| 2005/0147534 | A1 | 7/2005 | Swager et al. |

OTHER PUBLICATIONS

Sotomayor, N. et al. "Oxidation Reactions of 2'-Functionalized 3-Aryltetrahydro and 3,4-Dihydroisoquinolines," Tetrahedron 51, pp. 12721-12730, 1995.*

Thanh Hguyen Le, et al., A Versatile Total Synthesis of Benzo[c]phenanthridine and Protoberberine Alkaloids Using Lithiated Toluamide-Benzonitrile Cycloaddition, J. Org. Chem. 2004, 69, 2768-2772.

* cited by examiner

*Primary Examiner* — Yelena G Gakh  
*Assistant Examiner* — Michelle Adams  
(74) *Attorney, Agent, or Firm* — Timothy P. Evans

(57) ABSTRACT

A "real time" method for detecting chemical agents generally and particularly electrophilic and nucleophilic species by employing tunable, precursor sensor materials that mimic the physiological interaction of these agents to form highly florescent berberine-type alkaloids that can be easily and rapidly detected. These novel precursor sensor materials can be tuned for reaction with both electrophilic (chemical species, toxins) and nucleophilic (proteins and other biological molecules) species. By bonding or otherwise attaching these precursor molecules to a surface or substrate they can be used in numerous applications.

9 Claims, 2 Drawing Sheets

US 8,802,444 B1

DETECTION OF ELECTROPHILIC AND NUCLEOPHILIC CHEMICAL AGENTS

CROSS-REFERENCE TO RELATED APPLICATIONS

This application is a divisional application of and discloses subject matter this is related to subject matter disclosed in parent application U.S. Ser. No. 11/983,500 filed Nov. 9, 2007 and entitled "DETECTION OF ELECTROPHILIC AND NUCLEOPHILIC CHEMICAL AGENTS." The present application claims the priority of its parent application. The parent application is incorporated herein by reference. The parent application is a continuation application of U.S. Ser. No. 11/416,667 entitled "DETECTION OF ELECTROPHILIC AND NUCLEOPHILIC CHEMICAL AGENTS" (now U.S. Pat. No. 7,449,579).

STATEMENT OF GOVERNMENT INTEREST

This invention was made with Government support under Contract No. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

FIELD OF THE INVENTION

This invention is directed to a method for the detection of chemical agents generally and, in particular, to the detection of electrophilic and nucleophilic species including chemical and biological warfare agents by reaction with precursor sensor materials to produce readily detectable fluorescent berberine-based alkaloids.

BACKGROUND OF THE INVENTION

Rapid and sensitive detection of chemical warfare and biological agents have been an area of growing interest and importance. There are many current approaches toward chemical warfare agent (CWA) detection such as ion mobility spectroscopy (Cottingham, K. *Anal. Chern.* 10/1103, 435A439A), surface acoustic wave (Williams D.; Pappas G. *Field Anal. Chern. Technol.* 1999, 3, 45-53), microcantilever (Yang Y; Ji H-F.; Thundat T. *J. Arner. Chern. Soc.* 2003, 125, 1124-1125) and interferometric devices (Sohn H.; Letant S.; Sailor M. J.; Trogler W. C. *J. Arner. Chern. Soc.* 2000, 122, 5399-5400). While some of these methods show CWA simulant detection at low concentrations, specificity and discrimination among chemical threat agents is still lacking. Swager (Zhang S-W.; Swager T. M. *J. Arner. Chern. Soc.* 2003, 125, 3420-3421) has disclosed a novel fluorescent chemical detection method that yielded fluorescent species upon reaction with CWA simulants. However, Swager's chemical sensors do not allow for chemical modification amenable to a broad range of analytical platforms and suffer from low Stokes shifts (65 nm) with significant overlap of exciting light absorption and fluorescent emission. This effect results in low detection sensitivity to CWA simulants. Slow kinetics also limits sensitivity. Furthermore, it is important that the detection method or materials used allow for integration into multiple analytical platforms.

Moreover, long-wavelength fluorogenic chemical sensors that are reactively activated by biological agents do not exist. Fluorescent markers (e.g. green fluorescent protein and derivatives) currently used in cell biology are costly and suffer from background fluorescence from unreacted probes in experiments designed to detect molecular interactions.

SUMMARY OF THE INVENTION

The instant invention takes advantage of the observation that certain materials, hereinafter referred to as "'precursor sensor material(s)", "chemical sensor materials", "precursor molecule(s)" or "sensor molecule(s)" will react with both electrophilic (chemical species, toxins) and nucleophilic species (amino acids, peptides, proteins and other biological molecules) to form highly fluorescent compounds and thus, can be used to detect very low concentrations of chemical agents particularly hazardous chemical and biological materials and especially chemical and biological warfare agents.

Accordingly, the invention is directed, inter alia, to a "real time" method for detecting the presence of chemical and biological warfare agents by employing tunable, precursor sensor materials that mimic the physiological interaction of these agents to form highly florescent berberine-type alkaloids that can be easily and rapidly detected. For more general applications these novel precursor sensor materials can be tuned for reaction with both electrophilic and nucleophilic species. It is postulated that the molecules that constitute the chemical sensor materials react with a target species to transform two out-of-plane, weakly conjugated, short-wavelength sensor molecules into one rigid, planar, conjugated, chromophore with strong long wavelength fluorescence (530-560 nm,) and large Stokes shift (100-180 nm). Fluorescence intensity, reactivity, wavelength, and Stokes shift can all be tuned through altering the substituents on the chemical sensor molecule.

Synthetic methodology and proof-of-principle have been demonstrated with representative electrophilic and nucleophilic chemical species.

DETAILED DESCRIPTION OF THE INVENTION

The method of the invention and materials described herein can be configured to detect an analyte that can be an electrophilic or nucleophilic material, in a liquid or a vapor. The invention operates generally by monitoring the optical properties of a precursor material that is transformed into a rigid, planar, conjugated, chromophore having strong long wavelength fluorescence (530-560 nm) and large Stokes shift (100-180 nm) by reaction with the analyte.

In this invention advantage is taken of the well-characterized optical properties of berberine-type alkaloids, namely, high fluorescence intensity and large Stokes shifts (Pavelka, S.; Smekal, E. *Collection Czech. Chern. Cornrnun.*, 41, 3175-69, 1976.), to detect chemical agents, both electrophilic and nucleophilic species, generally and, in particular, chemical and biological warfare agents, hereinafter referred to by the acronym (CWA). By employing a tunable, precursor sensor material that mimics the physiological interaction of a CWA to produce a highly florescent berberine alkaloid reaction product, the CWA can be easily and rapidly detected by spectroscopic means. The term "tunable" as employed herein means changing the character and/or position of various functionalities, such as, for example, methylene dioxy and methoxy groups, on the precursor sensor molecule, thereby affecting the fluorescence intensity and/or wavelength of the fluorescence emission and magnitude of the Stokes shift. A more complete listing of the structural and fluorescent property variations that can result from the incorporation of various functionalities can be found in Pavella (ibid.).

For the purpose of describing this invention the novel precursor sensor material can be represented by generic formula (1)

wherein, R represents a functionality or group that will react with chemical agents, particularly biological or chemical warfare materials, and can be thio-, hydroxy-, a protected ether including t-butyldimethylene ethert, or the isourea of carbonyldiimidazole. Fluourescence intensity, wavelength and Stokes shift of the berberine alkaloid reaction product can be tuned by altering the composition and position of the substituents on rings A and D (cf. formula 1). A preferred substituent on rings A and D is methyoxy and a particularly preferred substituent is methylene dioxy (as shown) as well as combinations thereof.

It is believed that where the functionality R is an alcohol the interaction between the functionalized precursor molecule and a CWA can be represented by the general reaction scheme below to form the fluorescent molecule pseudocoptisine.

Figure 1:
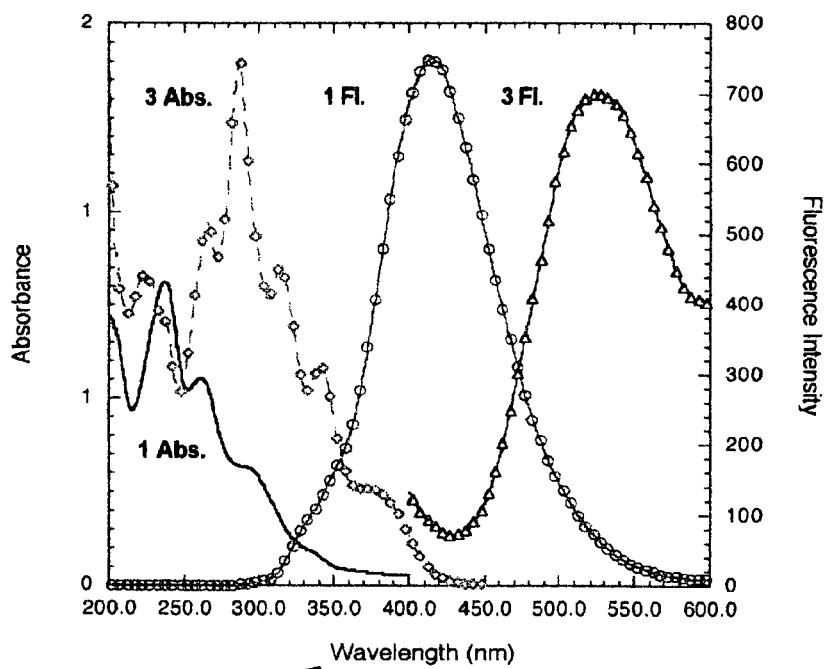
FIG. 1 shows the absorbance (Abs.) and fluorescence (Fl.) spectra of a precursor alcohol (1) and the reaction product pseudocoptisine (3).
Figure 2:
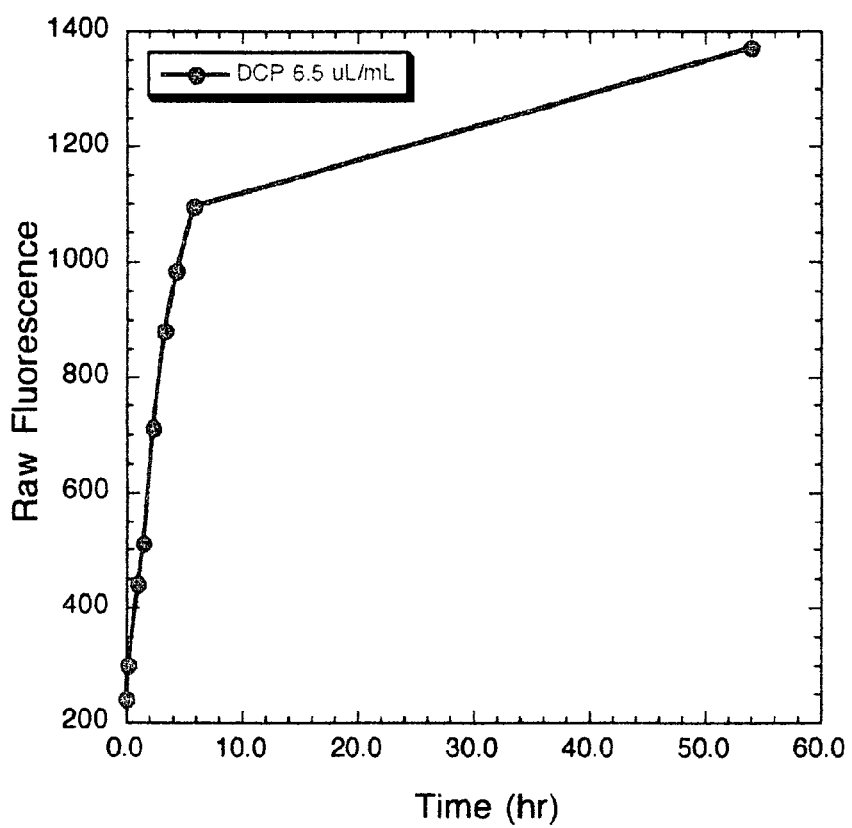
FIG. 2 shows raw fluorescence data for a precursor alcohol reacting with DCC.
Figure 3:
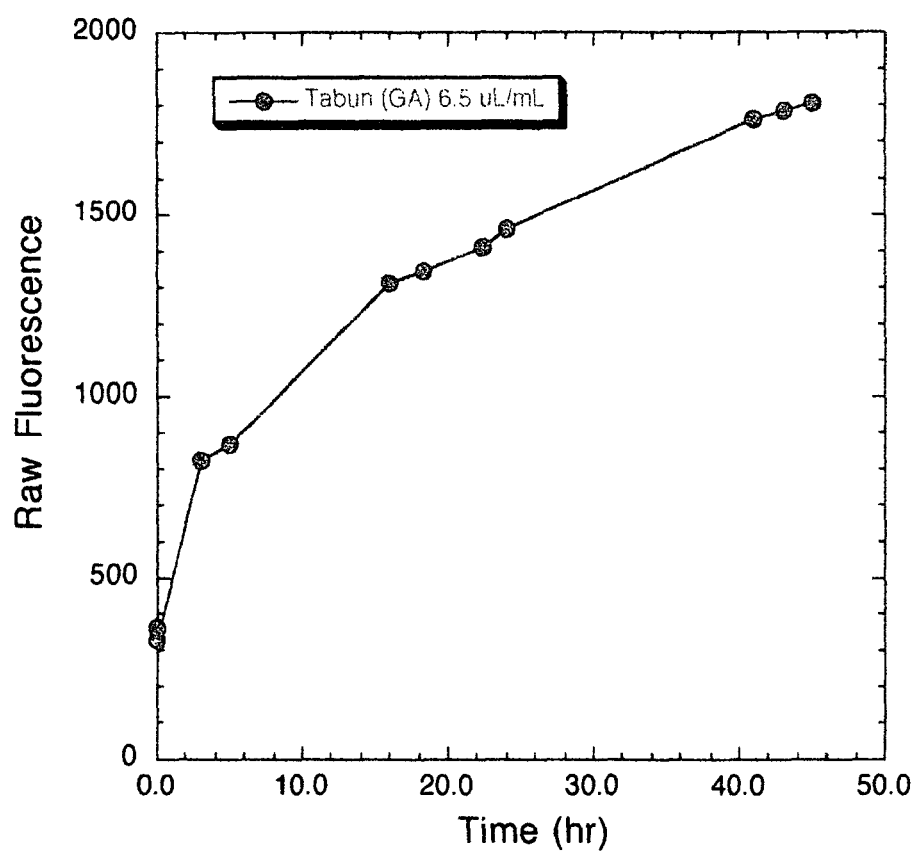
FIG. 3 shows the fluorescence data for an alcohol reacting with the nerve agent tabun.

In this proposed reaction scheme, once the precursor alcohol 1 reacts with a CWA an intermediate 2 is formed. This step is immediately followed by an intermolecular cyclization reaction resulting in a rigid planar, conjugated, highly delocalized chromophore 3, pseudocoptisine. As shown in FIG. 1, reaction product 3 has a Stokes shift of 176 nm and is highly fluorescent thereby allowing for unambiguous detection of a CWA.

It is recognized that for nucleophilic reactions and detection of bio-molecules, precursor molecule 1 can require activation of the alcohol functionality. Thus, in another aspect of the invention, a preliminary preparation step can be necessary for the detection of biological warfare agents. One preparation method can be the reaction of precursor sensor alcohol molecule 1 with carbonyldiimidazole CDI), which is a known cross-linker for cross-linking biological molecules (proteins, antibodies and DNA) and modifying polymeric substrates such as poly(vinylalcohol). Dicyclohexylcarbodiimide (DCC) can also be used in a similar fashion for the activation of precursor molecule 1. This process and the proposed subsequent reaction with a protein molecule is represented by the reaction scheme below in which activation is by the use of DCC.

Here, alcohol 1 is reacted with DCC to form O-alkyl isourea (1a). It is the intermediate isourea (1a) that when exposed to a biomolecule containing carboxylic acid functionalities cyclizes to form rigid planar, conjugated, highly delocalized chromophore 3. Reaction of 1a with the carboxylic acid functionality of a protein will result in the formation of molecule 1b and dicyclohexyl urea. Intramolecular ring closing of 1b forms a highly fluorescent reaction product pseudocoptisine 3.

Synthetic methodology for exemplary precursor sensor molecules 6,7-methylenedioxy-3-(3,4-methylenedioxy-6-vinyl-phenyl)-isoquinoline and 6,7-methylenedioxy-3-(3,4-methylenedioxy-6-ethanol isoquinoline is presented in the examples below.

EXAMPLE 1

Synthesis of 6,7-Methylenedioxy-3-(3,4-methylenedioxy-6vinylphenyl)-isoquinoline To a solution of 1,2-methylenedioxy-5-alkynyl-6-vinylbenzene in triethylamine (15 mL) was added $Pd(PPh_3)_2Cl_2$ (18.5 mg, 0.26 mmol) and CuI (2.3 mg, 0.12 mmol) and the reaction was stirred under Ar for 15 minutes. N-(4-iodobenzo[1,3]dioxol-6-yl)methylene)-tert-butylamine was added and the reaction stirred at 50 C under Ar until TLC ($SiO_2$, 114 ethyl acetate-petroleum ether) showed consumption of starting material. The reaction was filtered, the filtrate washed with diethyl ether (20 mL), and concentrated in vacuo. The crude imine-alkyne was used without farther purification or analysis. The residue was dissolved in $CHCl_3$, $AgN0_3$ (13.8 mg, 0.81 mmol) was added, and the reaction was heated and stirred under Ar at 50 C until TLC ($SiO_2$, 1/4 ethyl acetate-petroleum ether) showed consumption of starting material. The reaction was diluted with $CHCl_3$ and washed with brine. The organic layer was removed and the aqueous layer was extracted with $CHCl_3$, the organic layers combined, dried, and concentrated in vacuo. Column chromatography ($Si0_2$, 30/70 ethyl acetatepetroleum ether) of the residue yielded 6,7-methylenedioxy-3-(3,4-methylenedioxy-6-vinylphenyl)-isoquinoline in 26% yield as a yellow oil. IH NMR (500 MHz, $CDCl_3$) δ 9.08 (s, IH), 7.63 (s, IH), 7.41 (s, 1H), 7.26 (s, 1H), 7.20 (s, IH), 7.04 (s, 1H), 6.87 (dd, J=15.0, 10.0 Hz, IH), 6.20 (s, 2H), 6.06 (s, 2H), 5.66 (dd, J=15.0, 1.0 Hz, 1H), 5.08 (dd, J=10.0, 1.0 Hz, 1H).

EXAMPLE 2

Synthesis of 6,7-methylenedioxy-3-(3,4-methylenedioxy-6-phenylethanol)-isoquinoline To a solution of 6,7-methylenedioxy-3-(3,4-methylenedioxy-6-vinylphenyl)-isoquinoline (750 mg, 2.35 mmol) in anhydrous THF was added 1.0 M $BH_3$-THF (4.70 mL, 4.70 mmol). The reaction stirred at RT for 1 hour under Ar after which water (230 mL) was added dropwise followed by 3N NaOH (320 mL). Hydrogen peroxide (37%, 320 mL) was added dropwise and the reaction stirred for 1 hour at room temperature. Ethyl acetate (150 mL) was added to the reaction mixture, which was then washed with water (100 mL) and brine (100 mL). The organic layer was dried ($MgS0_4$) and the solvent removed in vacuo. Column chromatography ($Si0_2$, 70/30 ethyl acetate-petroleum ether) yielded 1 in 36% yield as a colorless solid. $^1H$ NMR (500 MHz, $CDCl_3$) δ 9.00 (s, IH), 7.63 (s, 1H), 7.22 (s, 1H), 7.10 (s, IH), 6.85 (s, 1H), 6.12 (s, 2H), 5.98 (s, 2H), 3.97 (t, J=6.0 Hz, 2H), 5.08 (t, J=6.0 Hz, 2H). $^{13}C$ NMR (125 MHz, $CDCl_3$) δ 151.91, 150.95, 148.82, 148.24, 147.71, 146.16, 135.76, 133.04, 132.75, 124.38, 120.48, 110.09, 109.96, 103.18, 102.61, 101.89, 101.25, 63.79, 35.29.

In order to better understand and appreciate its nature and scope, the present invention now will be described more fully hereinafter by way of various examples illustrative of the invention. This invention may, however, be embodied in many different forms and should not be construed as limited to the embodiments set forth herein but as defined by the appended claims.

EXAMPLE A

A solution of alcohol 1, i.e., 6,7-methylenedioxy-3-(3,4-methylenediox-6-ethanol-phenyl)-isoquinoline, was dissolved in DMSO to a $10^{-5}$M solution. About 20 μL of the chemical nerve agent simulant diisopropyl chlorophosphate (DCP) was added to about 3 mL of the alcohol solution. The reaction was monitored using a Barnstead International Turner Quantech Digital filter fluorometer incorporating a narrow band excitation filter at 360 nm and a 515 nm excitation filter. The Turner spectrometer was operated in a raw fluorescence mode. The fluorescence response/time data are shown in FIG. 2.

Solutions of nerve agent tabun (Edgewood Chemical and Biological Center) were prepared by adding 20 μL of neat agent to samples containing the chemical sensor 3 mL of 6,7-methylenedioxy-3-(3,4-methylenedioxy-6-ethanol-phenyl)-isoquinoline ($1.1\times10^{-4}$M). The reaction was monitored as in EXAMPLE A above. The Turner spectrometer was operated in raw fluorescence mode. The fluorescence response with time for reaction of the chemical sensor with tabun to form the reaction product pseudocoptisine is shown in FIG. 3.

Alcohol 1 (5 mg), i.e., 6,7-methylenedioxy-3-(3,4-methylenedioxy-6-ethanol-phenyl)-isoquinoline, was dissolved in deuterated $CH_2Cl_2$. CuCl (1 mg) and DCC (15 mg) i.e., dicylcohexylcarbodimide, was added and the reaction was monitored by $^1H$ NMR until complete. The solution was filtered, concentrated to dryness, dissolved in deuterated DMSO, and divided into two portions. The portions were then reacted with representative amino acids that are found in proteins. The first portion was reacted with aspartic acid (5 mg) and the second portion was reacted with lysine (5 mg). $^1H$ NMR revealed that each portion rapidly reacted with the amino acids to form psuedocoptisine 3 and exhibited the same spectral properties given in FIG. 2.

It is contemplated that the instant invention can be used in numerous applications by bonding or otherwise attaching the precursor chemical material to a surface or substrate. Tethering of the chemical sensor material to a substrate can be by means of substituents such as alcohols, thiols and/or polymerizable groups such as alkenes on rings A and D of the chemical sensor (cf. formula I).

In one embodiment of the invention the substrate can be a transparent amorphous polymer that would allow detection of a CWA or other chemical species in fluid samples such as sewage or industrial discharges.

In still another embodiment, the precursor chemical sensor materials can be incorporated into a fiber optic system having a flexible fiber optic probe such as described in U.S. Pat. No. 6,623,973 to Levitsky.

In yet another embodiment of the invention, the precursor chemical sensor materials disclosed herein can be incorporated into a handheld platform for field detection of CWA or biomolecules such as disclosed in U.S. patent application Ser.

No. 10/633,871, filed Aug. 4, 2003, now issued as U.S. Pat. No. 7,452,507, incorporated herein in its entirety.

What is claimed is:

1. A method for the detection of an electrophilic chemical agent comprising the steps of obtaining a precursor sensor molecule having the general formula:

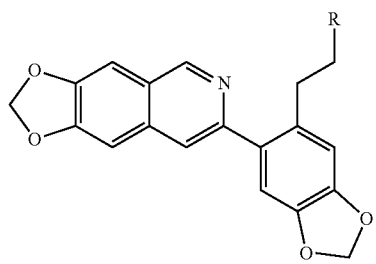

wherein R is a thio group or a hydroxyl group;
exposing the precursor sensor molecule to an environment; and
measuring a fluorescent signal generated by reaction of the precursor sensor molecule with the environment.

2. The method of claim 1, wherein the precursor sensor molecule is 6,7-methylenedioxy-3-(3,4-methylenedioxy-6-ethanol-phenyl)-isoquinoline.

3. The method of claim 1, further including immobilizing the precursor sensor molecule onto a surface.

4. The method of claim 3, wherein the surface is a surface of a transparent polymer material.

5. A method for the detection of a nucleophilic chemical agent comprising the steps of:
obtaining a precursor sensor molecule having the general formula:

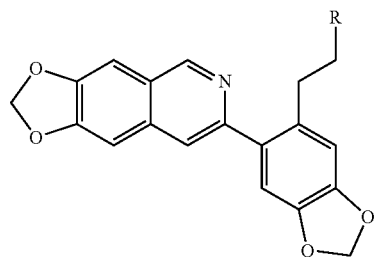

wherein R is a thio group or a hydroxyl group;
reacting the precursor sensor molecule with carbonyldiimidazole or dicyclohexylcarbodiimide to form an activated precursor sensor molecule;
exposing the activated precursor sensor molecule to an environment; and
measuring a fluorescent signal generated by reaction of the activated precursor sensor molecule with the environment.

6. The method of claim 5, wherein reacting the precursor sensor molecule comprises reacting with carbonyldiimidazole.

7. The method of claim 5, wherein reacting the precursor sensor molecule comprises reacting with dicyclohexylcarbodiimide.

8. The method of claim 5, further including immobilizing the precursor sensor molecule onto a surface.

9. The method of claim 8, wherein the surface is a surface of a transparent polymer material.

* * * * *